(12) United States Patent
Ahlberg et al.

(10) Patent No.: US 6,171,819 B1
(45) Date of Patent: Jan. 9, 2001

(54) ACYL TRANSFER WITH STABILIZED TRANSITION COMPLEX USING CATALYST WITH CATALYTIC IMIDAZOLE (E.G. HISTIDINE) FUNCTION

(75) Inventors: Per Ahlberg, Hovås; Lars Baltzer, Göteborg, both of (SE)

(73) Assignee: A + Science Invest AB, Göteborg (SE)

( * ) Notice: Under 35 U.S.C. 154(b), the term of this patent shall be extended for 0 days.

(21) Appl. No.: 09/180,670

(22) PCT Filed: May 13, 1997

(86) PCT No.: PCT/SE97/00780

§ 371 Date: Dec. 2, 1998

§ 102(e) Date: Dec. 2, 1998

(87) PCT Pub. No.: WO97/43302

PCT Pub. Date: Nov. 20, 1997

(30) Foreign Application Priority Data

May 14, 1996 (SE) .................................... 9601851
Sep. 12, 1996 (SE) .................................... 9603323

(51) Int. Cl.[7] ...................................... C12P 21/06
(52) U.S. Cl. ...................... 435/69.1; 528/327; 528/272; 528/289; 530/185.1
(58) Field of Search .................... 528/327, 272, 528/289, 292, 310, 322, 328, 331, 347, 363; 435/69.1; 530/185.1

(56) References Cited

PUBLICATIONS

Guthrie, JP, et al, "Hydration of acylimidazoles: tetrahedral intermediates in acylimidazole hydrolysis and nucleophilic attack by imidazole on esters. The question of concerted mechanisms for acyl transfers", Can J Chem vol 65, 1987, pp 1951–1969.*

Visser, HGJ, et al, "Synthesis of polymers of isocyanides derived from tripeptides containing imidazolyl, carboxyl, and hydroxymethyl groups", J Org Chem, 1985, 50, 3133–3137.*

Hajdu, J, et al, "Catalytic mechanisms of acyl transfer reactions in dipolar aprotic media 2. electrophilic activation of the carbonyl group by quarternary alkylammonium and imidazolium functions", J Am Chem Soc, 1981, 103, 6192–6197.*

Goren, HJ, et al, "Poly(L–histidyl–L–alanyl–aphal–L–Glutamic acid). II. Catalysis of p–Nitrophenyl acetate hydrolysis", Biopolymers, vol. 17, 1978, 1679–1692.*

Lee, S.G., et al, "Construction and expression of hybrid plasminogen activators prepared from tissue–type plasminogen activator and urokinase–type plasminogen activator genes", J Biol Chem, vol. 263, No. 6, 1988, pp. 2917–2924.*

Czugler M et al, "Noncovalent structural Imodels for the Asp–His dyad in the active site of serine proteases and for solid–state switching of protonation states", J Am Chem Soc, 1985, vol. 108, pp. 1275–1281.*

Li, Yishan et al, "Phospholipase A2 engineering. The Asp–His catalytic diad also plays an important structural role", J Am Chem Soc, Sep. 22, 1993, vol. 115, No. 19, pp. 8523–8526.*

Frey, PA, et al, "A low–barrier hydrogen bond in the catalytic triad of serine proteases", Science, vol.264, Jun. 24, 1994, pp. 1927–1930.*

Umeyama H et al, "Effects of the hydrogen bond between His57 and Asp102 on the lone pair molecular orbital of nitrogen of His57 in serine proteases", Chem Pharm Bull, vol.28, 1980, pp. 2292–2300.*

"Site–Directed Mutagenesis Reveals Transition–State Stabilization as a General Catalytic Mechanism for Aminocyl–tRNA Synthetases" Thor J. Borgford et al., *Biochemistry*, vol. 26, 1987, pp. 7246–7250.

"Transition State Stabilization by the High Motif of Class I Aminoacyl–tRNA Synthetases: The Case of *Escherichia coli* methionyl–tRNA Synthetase", Emmanuelle Schmitt et al., *Nucleic Acids Research*, vol. 23, No. 23, 1995, pp. 4793–4798.

* cited by examiner

Primary Examiner—John S. Brusca
Assistant Examiner—Stephen Siu
(74) Attorney, Agent, or Firm—Burns, Doane, Swecker & Mathis, L.L.P.

(57) ABSTRACT

The invention relates to a method of performing a chemical reaction between a reagent and a substrate, involving an acyl transfer mechanism, in the presence of an imidazole-based catalyst capable of forming a transition complex with the substrate. The catalytic imidazole function is provided by a chemical structure element comprising an optionally substituted imidazolyl group flanked on one or both sides by a group or groups capable of stabilizing the transition complex by molecular interaction with the acyl group. The invention also relates to such a designed chemical structure element, a method of producing it by recombinant DNA techniques and a vector therefor.

53 Claims, 3 Drawing Sheets

KO-42

ACYL TRANSFER WITH STABILIZED TRANSITION COMPLEX USING CATALYST WITH CATALYTIC IMIDAZOLE (E.G. HISTIDINE) FUNCTION

FIELD OF THE INVENTION

The present invention relates to the catalysis of chemical reactions, and more particularly to the catalysis of acyl transfer reactions.

BACKGROUND OF THE INVENTION

So-called acyl transfer reactions involve the transfer of an acyl group (the residue of an organic acid after removal of the carboxyl hydroxy group) either internally within a chemical species or from one chemical species to another. Examples are amide formation, transesterification and hydrolysis.

It is well known that acyl transfer reactions may be catalyzed by imidazole in aqueous solution, the imidazole, which is a strong nucleophile, forming an intermediary reactive complex with the acyl group. Also polymer-supported imidazoles have been used as acyl transfer catalysts (see e.g. Skjujins, A., et al., Latv. PSR Zinat. Akad. Vestis, Kim. Ser. 1988 (6), 720–5).

It has further been shown that small peptides containing a histidine (His) residue (an amino acid which contains an imidazolyl group) may have hydrolytic activity.

Recent progress in designing structural proteins and peptides have resulted in the preparation of several peptides with substantial catalytic activity (W. F. DeGrado, Nature, 365, 488 (1993). For example, K. Johnsson et al., Nature, 365, 530 (1993) disclose a short self-associating Leu-Lys-rich helical peptide that accelerates the rate of decarboxylation by means of a Schiff's base intermediate between a substrate of oxaloacetate and an amine with an electrostatically depressed acid constant ($K_a$). It is mentioned that the secondary structure is important for the activity.

The present invention provides improvements in designed catalytic structures including an imidazole-based catalytic function.

SUMMARY OF THE INVENTION

According to the present invention it has been found that the above described imidazole induced catalytic activity in acyl transfer reactions may be increased considerably if the imidazolyl moiety is provided in a chemical structure flanked on one or both sides by a group of such a nature and position that it is capable of stabilizing the transition complex formed between the imidazolyl group and the acyl group in question. To accomplish such a stabilization, the flanking group or groups should be capable of molecular interaction with the acyl complex, such as by hydrogen bonding, electrostatic or hydrophobic interactions or van der Waal forces (intramolecular polarization).

The increased catalytic activity may be used in combination with intermolecular as well as intramolecular reactions in solution, with and without stereospecifity. In the latter case it is possible to make site selective functionalization of peptides and other molecules. Such site selective functionalization will inter alia permit site selective immobilization of molecules, such as biomolecules, e.g. antibodies or other proteins or polypeptides.

One of the objects of the invention is to provide an improved method of performing an acyl transfer type reaction using an imidazole based catalyst.

In a first aspect of the invention, there is therefore provided an improved method of performing a chemical reaction involving an acyl transfer mechanism in the presence of an imidazole-based catalyst which can form a transition complex with the acyl group. The method is characterized in that the imidazole function is provided by a chemical structure element comprising an imidazolyl group flanked on one or both sides by a group capable of stabilizing the transition complex by molecular interaction with the acyl group. This molecular interaction may be selected from hydrogen bonding, electrostatic interaction and hydrophobic interaction.

In a preferred embodiment of the method, the chemical structure element constitutes or is part of a larger structure having a functional group in such a neighboring position that it can be site-specifically functionalized through the acyl transfer via the above intermediary complex.

Another object of the invention is to provide a chemical structure element with improved capability of catalyzing an acyl transfer reaction.

In a second aspect of the invention, there is therefore provided a chemical structure element comprising backbone structure with a pendant imidazole function, which element is characterized in that the imidazole function is flanked on one or both sides on said backbone structure by a pendant group capable of stabilizing the transition complex by molecular interaction with the acyl group.

In one embodiment, the structure element is a molecule, such as a peptide or protein, comprising a function in such a neighboring position that it can be site-specifically functionalized through the acyl transfer via the above intermediary complex.

Yet another object of the invention is to provide a method of producing by genetic engineering a protein or peptide constituting or comprising a structure element having an imidazole function flanked on one or both sides by a transition complex stabilizing group.

In a third aspect, the invention therefore provides a method of producing a protein or peptide which constitutes or comprises an imidazole function-containing structure element as defined above, which method comprises transforming a host organism with a recombinant DNA construct comprising a vector and a DNA sequence encoding said protein or peptide, culturing the host organism to express said protein or peptide, and isolating the latter from the culture.

In a preferred embodiment of the method, the structure element comprises a functional group in a such a neighboring position to the imidazole function that the function can be site-specifically functionalized through acyl transfer catalyzed by the imidazole function.

Still another object of the invention is to provide a vector comprising a nucleic acid sequence encoding the above protein or peptide.

In a fourth aspect, the invention therefore provides a recombinant DNA construct comprising a vector and a DNA sequence encoding a protein or peptide which constitutes or comprises an imidazole function-containing structure element as defined above.

In a preferred embodiment of the vector, the DNA sequence also encodes a specific functional group in a such a neighboring position to the imidazole function that the functional group can be site-specifically functionalized through acyl transfer catalyzed by the imidazole function.

The foregoing and other objects, aspects, features and advantages of the present invention will be more fully appreciated as the same become better understood from the following detailed description of the invention. Reference will be made to the accompanying drawings.

DETAILED DESCRIPTION OF THE INVENTION

Figure 1A:
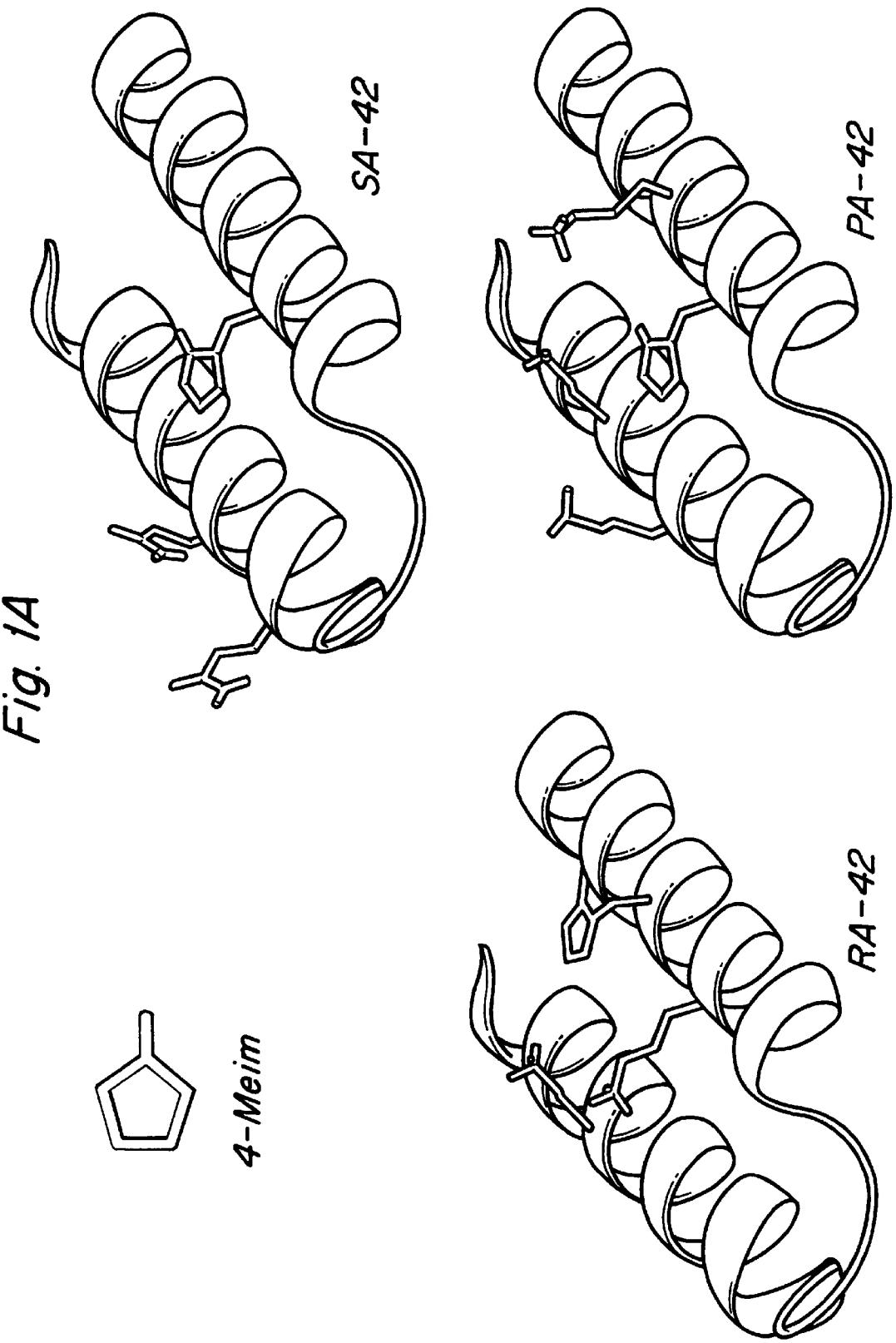
FIGS. 1A and 1B are schematic illustrations of helix-loop-helix structures of four designed polypeptides, viz. SA-42, RA-42, PA-42 (FIG. 1A) and KO-42 (FIG. 1B), with their designed reaction centers indicated.

As mentioned above, the present invention is based on the concept of increasing the imidazole type catalytic activity in acyl transfer reactions by providing the imidazole function on a backbone structure with a pendant flanking group or chain on one or both sides of the imidazole function, which flanking group or groups can interact with the imidazole-acyl complex formed such that the transition complex is stabilized. As will be explained further below, the reaction rate for the desired acyl transfer reaction, such as an amidation, trans-esterification, hydrolysis or thiolysis, will be increased considerably thereby. While esters are the currently preferred substrates, e.g. amide and anhydride substrates may also be contemplated.

The term "imidazole function" is to be interpreted broadly herein, and is meant to encompass any imidazolebased structure that possesses the desired catalytic activity. The imidazole group may consequently be modified in various ways. An advantageous imidazole function For many purposes is based on the amino acid histidine (α-amino-4-(or 5)-imidazolepropionic acid). One or both of the available carbon atoms of the imidazole function may, for example, be independently substituted with alkyl or halogen. The imidazole group may also be substituted in 1-position with alkyl. Alkyl has preferably 1 to 6 carbon atoms, especially 1 to 4 carbon atoms, e.g. methyl or ethyl. Halogen includes fluorine, chlorine, bromine and iodine.

The flanking group or groups may comprise a link or chain of, e.g., 1 to 6, preferably 1 to 4 atoms, usually carbon atoms, connected to a terminal functional group or other group capable of the required molecular interaction with the acyl transition complex.

In case the catalytic structure element is a peptide and the imidazolyl function is part of a histidine residue, the flanking chain or chains may be pendant proton donating parts of other amino acids, e.g. selected from lysines, ornithines, arginines and/or further histidines.

The chemical structure element supporting the catalytic imidazolyl function should preferably have some type of rigidity, such as secondary structure, in order to localize the flanking group or groups with respect to the imidazolyl function in an optimal geometric relationship for the desired transition complex-stabilizing interactions to take place. In an advantageous embodiment, the chemical structure element is a so-called designed polypeptide with a stabilized secondary structure, e.g. α-helical coiled coils. Designed helical peptides are, for instance, described in J. W. Bryson et al., Science, 270, 935 (1995). The structure element is, however, not limited to a peptide. On the contrary, it may have any of a variety of compositions readily apparent to the skilled person in the light of the present invention, and may thus be included in or be part of other types of structures, such as a carbohydrate, a natural or synthetic polymer, etc. The size of the chemical structure is not either limiting, and it may, e.g., be a peptide of as few as, say, five amino acids. As to the required geometric relationship between imidazole function and flanking group or groups, a functional arrangement may readily be designed for each particular situation by the skilled person after having read the present description.

Depending on the functional moiety of the complex-stabilizing flanking chain or chains, the transition complex may react with such a flanking chain in an intra-molecular reaction. Such an intramolecular reaction may be used for selectively functionalizing peptides, proteins and other molecules. An example of such an intra-molecular reaction is outlined in the reaction scheme below.

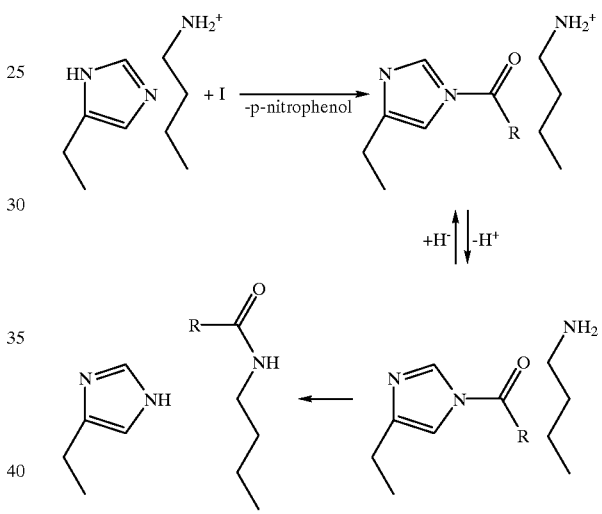

In the above scheme, the imidazolyl structure is part of a histidine (His) residue and the aminopropyl chain is part of an ornithine (Orn) residue, both included in a designed α-helical polypeptide at a distance of four carbon atoms from each other (i.e. at positions "i" (His) and "i+4" (Orn)), the His and Orn residues thereby being located on the same side of the helix (4 carbon atoms in each coil). "I" represents an active ester, here specifically mono-p-nitrophenylfumarate. The reaction is performed at a pH value where the ornithine amino group is almost completely protonated and thereby unavailable for direct reaction with the active ester. An example of such an α-helical polypeptide is RA-42, the supersecondary structure of which is schematically shown in FIG. 1A. RA-42 has 42 amino acids, and His-15, Orn-15 and Orn-34 residues. The polypeptide RA-42 will be described in more detail in the Experimental part below.

The reaction starts with an initial attack of the imidazole residue of His on the active ester to form an acyl intermediate with release of p-nitrophenol. The acyl intermediate is stabilized by the ornithine side chain which may flex towards the acyl complex to interact therewith through hydrogen bonding between the protonated amino group and the developing oxyanion of the acyl group. The acyl group is then transferred from the histidine residue to the ornithine residue, free histidine being regenerated.

It is possible to have an additional stabilizing chain on the opposite side of the histidine residue. The resulting transition complex formed is schematically illustrated below.

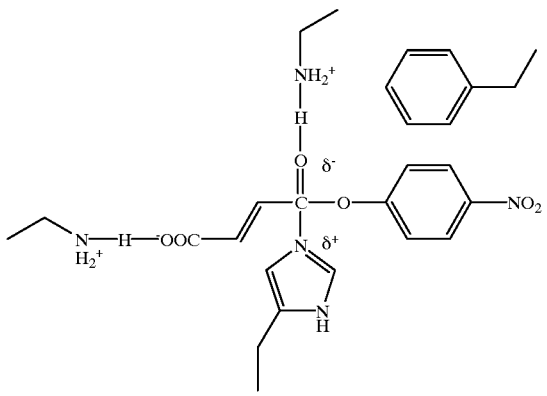

It has been found that a particularly increased catalytic activity is obtained when the histidine residue is flanked by two other histidine residues (In the case of an α-helix, in positions i+4 and i−4).

Relative to a histidine residue in position if acylation may also take place in position i−3 (but not in positions i−4, i−1, i+2 and i+3).

Exemplary groups for i+4 acylation are, in addition to ornithine mentioned above, lysine and 1,3-diamino-butyric acid, while i−3 acylation may be exemplified by lysine.

Furthermore, there may be functional groups both at position i+4 and position i−3, and the functional groups in this case are e.g. lysines.

It is also possible to use structural elements with more than one imidazolyl function in positions i, j, k etc., and these functions may then be flanked on one side or on both sides by functional groups, preferably at positions i+4, j+4, k+4 etc., and i−3, j−3, k−3 etc., respectively.

It is thus possible to catalyze acyl transfer reactions using e.g. functionalized helix-loop-helix motifs designed from simple principles of transition state binding, the favorable complex stabilization being obtained by the introduction of e.g. positively charged hydrogen bond donors that interact with negatively charged substrates in a predictable way. In the above case, the main binding interaction in the transition state is that to the developing oxyanion of the ester functional group. That is shown by the fact that p-nitrophenylacetate, that has no negatively charged functional group, is catalyzed with almost the same efficiency as mono-p-nitrophenylfumarate, as will be demonstrated in the Experimental part below.

It is readily understood that designed polypeptides embodying the present invention, such as those mentioned above, may be produced by recombinant DNA technology (genetic engineering). Such techniques are well known and to the skilled person and will not be described herein. (It may, for example, be referred to EP-B1-282 042 which discloses the preparation by recombinant technology of fusion proteins which contain neighboring His-residues.)

The above described selectivity of the reaction center may be used to introduce new functionality in e.g. folded polypeptides. In an intramolecular reaction, the stabilizing flanking group(s) need, of course, not be the one to be functionalized through the acyl transfer but may be another functional group in an appropriate position.

An important aspect of site-selective functionalization is the introduction of carbohydrates site-selectively into proteins and peptides. This is accomplished by modifying the carbohydrate in question to contain an ester function. Carbohydrates play an important role in the recognition in immunological, inflammatory and other processes. They also protect proteins from proteolytic degradation and affect protein folding. Site-selective introduction of carbohydrates may therefore be used for the systematic study or the role of carbohydrates. It can also be used to protect drugs from degradation.

The method according to the invention can be used to develop vaccines, to mimic components of the immune system, and to construct antagonists and agonists for components of the immune system.

The method of the invention can also be used for the stepwise introduction of diverse functionality at different positions if different reactivity in the side chains is provided. It is understood that such reactions will have great potential in site-selective immobilizations and in the construction of functionalized polypeptides, such as novel catalysts, introduction of co-factors etc.

An example of site-selective immobilization is schematically illustrated below where a designed polypeptide of the above-mentioned helix-loop-helix type, which has a catalytic histidine residue in a stabilizing relationship with a flanking aminoalkyl chain, is immobilized via the amino function to an ester function ($R_1OCO$) of a solid support. The reaction is carried out at such pH conditions that all amino functions are almost completely protonated and thereby unavailable for direct reaction with the ester function.

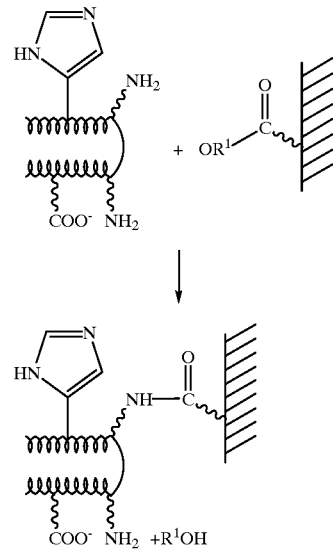

Immobilization to a solid support may, of course, be effected the other way round, i.e. by providing the histidine residue and the amino function on the solid support and the ester function on the peptide.

The reaction may also be used to introduce residues that will not survive under the reaction conditions of peptide synthesis or that will not be reactive enough due to steric hindrance. Novel branched polypeptide structures are also possible if amino acid residues or peptides can be introduced. Since the histidine is regenerated, it can also be designed to participate in the active site of an engineered catalyst. Further possible applications include construction of peptide libraries with peptides having a secondary or tertiary structure for specific binding of e.g. a substrate or a receptor; construction of polypeptides for specific non-covalent binding of endogenous substances in the blood circulation; in allergy diagnoses (and clinics) as well as immunology; construction of molecules having topologies for antibody production; and vaccine production.

The invention will now be described in more detail with regard to experiments performed on some specific designed polypeptides.

EXPERIMENTAL

Synthesis of Catalytic Polypeptides SA-42, RA-42, PA-42, LA-42 and KO-42

The amino acid sequences of polypeptides SA-42, RA-42, PA-42 and KO-42 are shown in the Sequence Listing provided at the end of the description. The residues presented underlined in bold for RA-42, PA-42 and KO-42 are the ones designed to constitute the catalytic binding site. The one letter code for amino acids is used where A is Ala, D is Asp, E is Glu, F is Phe, G is Gly, H is His, I is Ile, K is Lys, L is Leu, N is Asn, P is Pro, Q is Gln, R is Arg, V is Val. Aib is α-aminoisobutyric acid and Nle is norleucine.

Figure 1B:
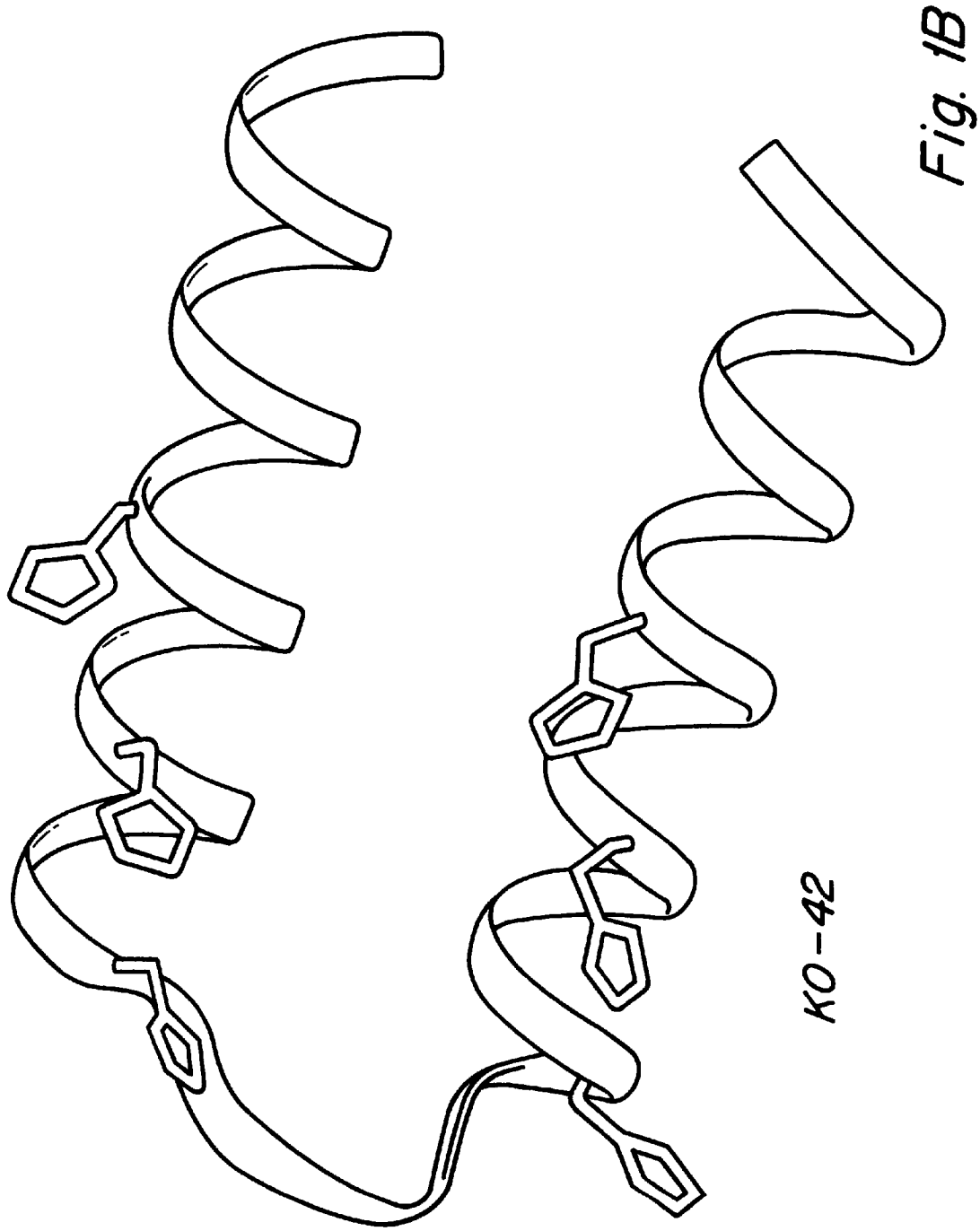

As can be seen in the Sequence Listing, as well as from FIGS. 1A and 1B, the polypeptides are helix-loop-helix motifs. In solution the peptides dimerise to form four-helix bundles, but for simplicity only the monomer is shown.

LA-42 (not shown) is identical to RA-42 except that Orn-15 is replaced by Lys-15.

SA-42 was synthesized as described by Stewart, J. M., and Young, J. D., Solid Phase Peptide Synthesis, Pierce Chem. Co. Pockford, Ill. 1984. Polypeptides RA-42, PA-42, LA-42 and KO-42 were prepared in the same manner with the exception of the amino acid derivatives used at the modified positions. The side-chain protection group of ornithine was 2-Cl-CBZ (2-chloro-carbobenzoxy-carbonyl).

The polypeptides were synthesized on an automated peptide synthesizer (Biosearch 9600), using t-BOC protection groups and phenylacetamidomethyl-(PAM) linked resins. They were cleaved from the resin by anhydrous HF on a Teflon vacuumline (Peptide Institute Inc.) and purified by size-exclusion chromatography and reversed-phase and ion-exchange HPLC. Electro-spray mass spectrometry (VG Analytical, ZabSpec) and amino acid analysis were used to establish the identity of the peptides and the purity was checked by HPLC.

Synthesis of mono-p-nitrophenylfumarate

Freshly distilled fumaryl chloride (0.9 g, 5.9 mmol) was dissolved in 100 ml of acetone and allowed to react with the residual water of the solvent for 30 min. A small portion (0.2 ml) was transferred to a dry round bottom flask and the solvent evaporated. The residual mixture was dissolved in $CDCl_3$ and transferred to an NMR tube. The $^1H$ NMR spectrum showed a mixture of fumaryl chloride (7.10 ppm, s) and partly hydrolyzed fumaryl chloride (6.998 and 7.07 ppm, dd, J=16 Hz). Fumaric acid is only sparingly soluble in chloroform. Water was then added to the acetone solution and the NMR analysis was repeated. A total of 54 µl (3 mmol) were added in small portions with a syringe, and after each addition, the degree of reaction was analyzed by NMR spectroscopy. When the solution contained no more fumaryl chloride, the acetone was evaporated and the remaining oil was dissolved in 50 ml ethanol-free chloroform and centrifuged to remove fumaric acid. The supernatant was transferred to a round bottom flask and 1.8 g of freshly prepared sodium p-nitrophenolate, dried under heating in vacuo until it turned bright orange, was added. The slurry was allowed to react with stirring overnight and was then centrifuged. The solid material was extracted with 3×50 ml of water and the combined aqueous phase was titrated to pH 6 with 0.3 M acetic acid and extracted with 5×30 ml of $CH_2Cl_2$ to remove the p-nitrophenol. The aqueous phase was titrated to pH 4.3 with 0.3 M acetic acid and extracted with 5×30 ml of $CH_2Cl_2$. The combined organic phase was allowed to stand overnight at 255 K. A small crop of crystals (40 mg) was collected and after partial evaporation of the solvent in a stream of dry nitrogen, a second crop was collected (60 mg) consisting of the desired product, mono-p-nitrophenylfumarate. No attempts were made to optimize the yield. The product was identified from NMR spectroscopy and from mass spectrometry.

Measurement of Second Order Rate Constants for the Acyl Transfer Reaction of mono-o-nitrophenyl-fumarate as Well as of Other Substrates The second order rate constants for the acyl transfer reaction of mono-p-nitrophenylfumarate was determined for the following substances: polypeptides SA-42, RA-42, PA-42, LA-42 and KO-42, and 4-methylimidazole.

The kinetic measurements were carried out at 290.2 K in 10% (v/v) trifluoroethanol (TFE), 90% 100 mM Bis-Tris buffer or in aqueous buffer solution at pn 4.1, 5.1 or 5.85 by following the increase in absorbance at 320 nm using a Cary 4 spectrophotometer equipped with a Cary temperature controller. The substance to be measured was dissolved in 300 µl of buffer solution and titrated to the relevant pH by 0.1 M NaOH in 10% TFE solution and centrifuged. 300 µl of clear substance solution was transferred to a 1 mm, UV cuvette and placed in the thermostatted compartment of the UV spectrometer. The substrate was weighed and dissolved in buffer solution and 20 µl was transferred to the cuvette by a pipette and the reaction started. The concentrations of the peptides were determined by quantitative amino acid analysis and each rate constant was the average of two runs. Each kinetic run was followed for at least two half-lives and a single exponential function of the form $A+A1^*e^{-kt}$ was fitted to the data. Under conditions of excess peptide, each peptide solution was used for two runs and to start the second reaction a second portion of 20 µl was added to the cuvette. In the case of RA-42 where the excess rate enhancement was lost upon reaction with the substrate, the concentration of peptide in the second run was corrected for the loss of reactive peptide. The total concentration of substrate was 0.13 mM and the corrections of the second order rate constants were small, less than 10%. The same correction was applied to the rate constants of PA-42. The rate constants and relative rates obtained in 10% TFE at pH 5.85 are presented in Table 1 below where also the corresponding data for the bimolecular reaction between mono-p-nitrophenylfumarate and trifluoroethanol are given.

TABLE 1

| Catalyst | Rate constant $s^{-1} M^{-1}$ | Relative rate |
|---|---|---|
| SA-42 | $5.3 * 10^{-3}$ | 331 |
| RA-42 | $2.8 * 10^{-2}$ | 1750 |
| PA-42 | $3.1 * 10^{-2}$ | 1937 |
| KO-42 | $2.6 * 10^{-1}$ | 16250 |
| LA-42 | $5.6 * 10^{-2}$ | 3500 |

TABLE 1-continued

| Catalyst | Rate constant $s^{-1} M^{-1}$ | Relative rate |
|---|---|---|
| 4-Methylimicazole | $3.4 * 10^{-3}$ | 211 |
| Mono-p-nitrophenyl-fumarate and TFE | $1.6 * 10^{-5}$ | 1 |

As shown in the table, a considerable increase of the rate constant is obtained for the peptides RA-42, PA-42 and KO-42, i.e. these peptides exhibit a remarkably enhanced catalytic activity as compared with 4-methylimidazole and the peptide SA-42. The increased catalytic activity is due to she previously described stabilization of the transfer complex. Thus, all three peptides have a positively charged hydrogen bond donor in such a geometric position that it can stabilize the complex between the His function and the acyl group, or rather the developing oxyanion of the acyl group. Thus, RA-42 has a catalytic His in position 11 and a stabilizing Orn in position 15. PA-42 has a His in position 15 and a stabilizing Orn in position 11. KO-42 has His-residues in positions 11, 15, 19, 26, 30 and 34. SA-42, on the other hand, has a His-15 residue but no stabilizing function. As will be described below, the reaction product in the RA-42 catalyzed reaction is the amide formed at the side chain of Orn-15 (amidation). In the 4-methylimidazole catalyzed reaction it is the TFE ester (transesterification).

In a corresponding study to that described above, the acyl transfer of mono-p-nitrophenylfumarate catalyzed by the polypeptide KO-42 and 4-methylimidazole (4-MeIm), respectively, was compared to the reaction between mono-p-nitrophenylfumarate and trifluoroethanol (TFE). The reactions were carried out at pH 4.1 in 10% (v/v) trifluoroethanol, 90% 100 mM sodium acetate buffer at 290 K, the reaction product being the TFE ester (transesterification). The results (rate constants and relative rates) are shown in Table 2 below.

TABLE 2

| Substrate | Rate constant $s^{-1} M^{-1}$ | Rel. rate |
|---|---|---|
| KO-42 | $5.0 * 10^{-2}$ | 156250 |
| 4-MeIm | $7.90 * 10^{-5}$ | 247 |
| Mono-p-nitrophenyl-fumarate and TFE | $3.2 * 10^{-7}$ | 1 |

In an analogous manner, the acyl transfer to hydroxide ion (hydrolysis) catalyzed by the polypeptide KO-42 and 4-methylimidazole (4-MeIm), respectively, was studied at pH 5.1 in 100 mM sodium acetate buffer at 290 K on the following substrates: mono-p-nitrophenyl-fumarate, p-nitrophenylacetate, cyclopentanedicarboxylic acid mono-p-nitrophenyl ester, and D- and L-tryptophane-p-nitrophenyl ester. The results are shown in Table 3 below.

TABLE 3

| Substrate | KO-42 $s^{-1} M^{-1}$ | 4-MeIm $s^{-1} M^{-1}$ | Rel. rate |
|---|---|---|---|
| Mono-p-nitro-phenyl fumarate | 0.31 | $7.4 * 10^{-4}$ | 419 |
| p-Nitrophenyl-acetate | 0.29 | $7.2 * 10^{-4}$ | 402 |
| Cyclopentane-1,2-di-carboxylic | 0.86 | $1.5 * 10^{-3}$ | 573 |

TABLE 3-continued

| Substrate | KO-42 $s^{-1} M^{-1}$ | 4-MeIm $s^{-1} M^{-1}$ | Rel. rate |
|---|---|---|---|
| acid mono-p-nitrophenyl ester | | | |
| Tryptophane p-nitrophenyl ester (D- and L-) | 3.7 | $5.5 * 10^{-3}$ | 540 |

Self-catalyzed Site-selective Functionalization of Polypeptides RA-42 and LA-42

Polypeptide RA-42 prepared above (see Sequence Listing) folds in solution into a hairpin helix-loop-helix motif. It has a designed reaction center which includes His-11, Orn-15 and Orn-34 based on determination by NMR and CD spectroscopy. RA-42 was reacted with mono-p-nitrophenylfumarate. The final reaction product was an amide at the side chain of Orn-15, as determined by electrospray mass spectroscopy and NMR spectroscopy.

The reaction was studied at 0.5–1 mM concentration of peptide. It was found that His-11 catalyses the acyltion of the side chain of Orn-15 in a self-functionalization reaction, leaving other amino groups unfunctionalized. As will be further described below, the reaction mechanism includes the formation of an acyl intermediate with His-11, which is followed by a site selective acyl group transfer from His-11 to Orn-15.

In an analogous manner, the p-nitrophenyl ester of N-methyl nicotine acid was reacted with RA-42 with the above described technique to worm the corresponding nicotine amide.

In an analogous manner, the galactose-derived p-nitrophenyl ester of the formula

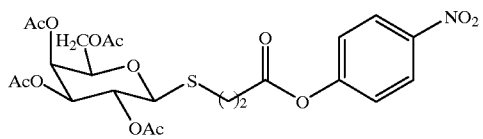

was reacted with the polypeptide LA-42 with the above-mentioned technique in aqueous solution at pH 5.85 to form the corresponding amide. Identification of the reaction product (the tetraacetyl derivative) was performed by electrospray mass spectrometry (ES-MS). The acetyl groups are removed by hydrolyzis in aqueous solution. The p-nitrophenyl ester used in the reaction was prepared by standard dicyclohexylcarbodiimide coupling of the corresponding carboxylic acid and p-nitrophenol.

Study of Reaction Mechanism

As shown in Table 1 above, the second-order rate constant of RA-42 is $2.8*10^{-2}$ $M^{-1}s^{-1}$ in 10 volt % TFE at pH 5.85 which is more than 1000 times greater than that of the comparable reaction between ethylamine and p-nitrophenylacetate (Knowles, J. R., et al., J Chem. Soc. Commun., 1967, 755–757). As also shown in Table 1, the His-11 catalyzed reaction of RA-42 is 8.3 times fester than that catalyzed by 4-methylimidazole at the same conditions. In aqueous solution the second-order rate constant for RA-42 was found to be $5.07*10^{-2}$ $M^{-1}$ $s^{-1}$, and for 4-methylimidazole, $1.05*10^{-2}$ $M^{-1}s^{-1}$, i.e. the observed rate enhancement, about a factor 5, is almost the same as in 10 vol % TFE.

Figure 2:
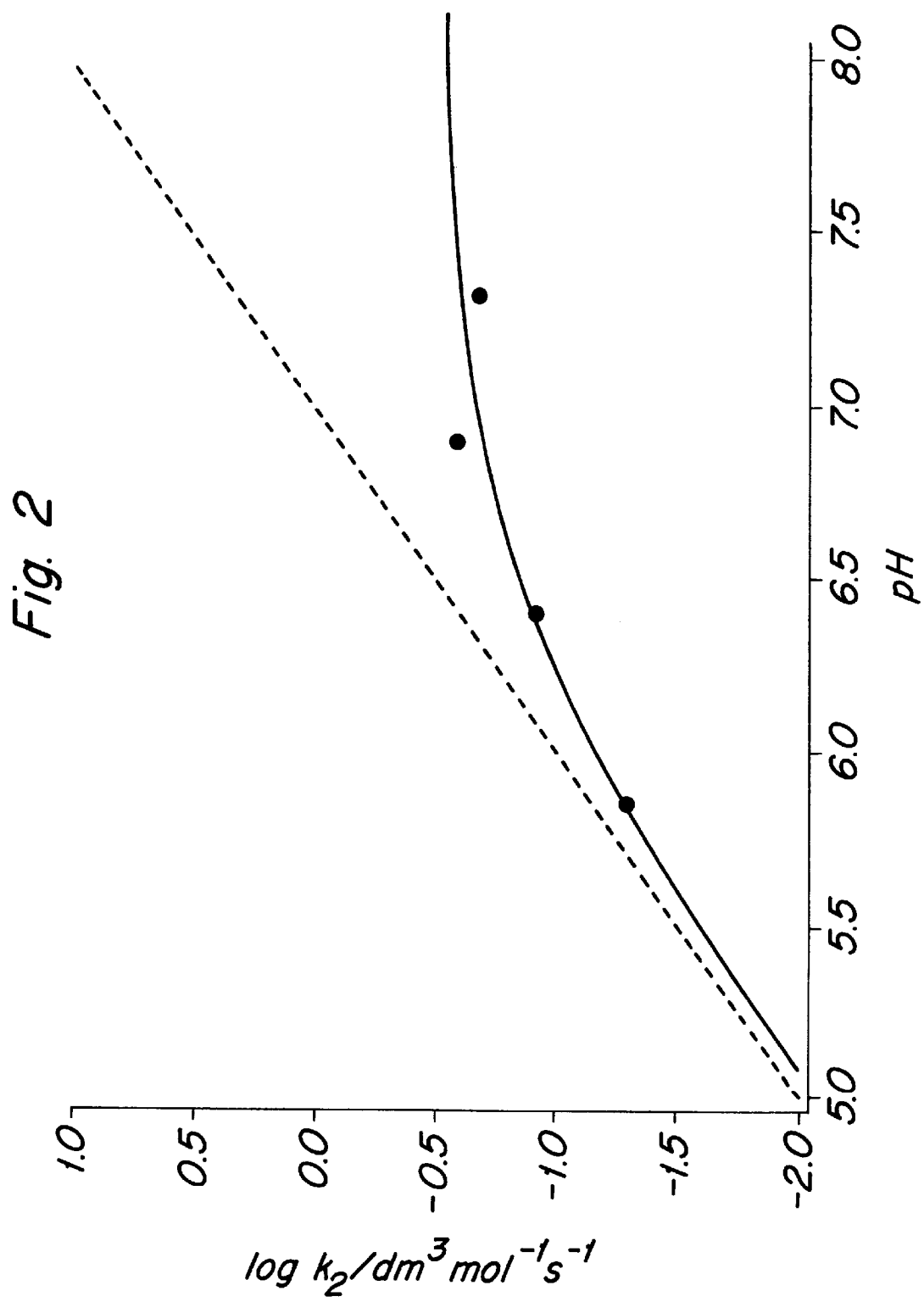
FIG. 2 is graph showing the logarithm of the second-order rate constants for the release of p-nitrophenol versus pH by an acyl transfer reaction between mono-p-nitrophenylfumarate and an imidazole-containing structure according to the present invention (RA-42). The dotted line shows the expected dependence on pH of the rate constant of a reaction catalyzed by the deprotonated form of ornithine with a pKa of 10.4.

The pH dependence of the second-order rate constants for the acyl transfer reaction was measured in 50 mM Bis-Tris buffer at 290.2 K. A plot of the logarithm of the second-order rate constants versus pH is shown in FIG. 2. The reaction is first order with respect to concentration of peptide. As can be seen from FIG. 2, the second-order rate constants increase with pH which indicates that the reaction depends on an amino acid residue in its deprotonated form. If the products were formed in a direct reaction between Orn-15 and the p-nitrophenylfumarate, the logarithm of the second-order rate constants would show a linear dependence on pH in the range from 5 to 8, as the pKa of the side chain of the ornithine residue probably is between 10 and 11 (Tanford, C., Adv. Protein Chem. 1962, 17, 69–165). However, the observed pH profile rules out that mechanism and indicates that the reaction depends on an an amino acid residue with a pKa close to 6.5.

The amino acid sequence of RA-42 contains the ionizable residues Asp, Glu, Arg, Orn, Lys and His, as well as the C-terminal carboxylic acid and the N-terminal amino group of the peptide backbone. Typical pKa's of ionizable amino acid residues in small peptides have been determined (Tanford, C., 1962, supra), and the only amino acid in RA-42 with a pKa value close to 6.5 is His with a pKa of 6.4. The pKa of the corresponding acid of the side chain of His-11 was determined by $^1$H NMR spectroscopy (Varian Unity 500 NMR spectrometer operating at 290 K by measuring the chemical shifts of the histidine aromatic protons as a function of pH) and it was found to be 6.55 in aqueous solution. Therefore, it may be concluded that an initial acyl transfer reaction of p-nitrophenyl-fumarate by initial attack of His-11 gives rise to an acyl intermediate and a reactive imidazolide is formed. The observed p.H dependence also shows that the first step is rate limiting.

The pKa of the 4-methylimidazolium ion has been determined and was found to be 7.95 in aqueous solution at 303 K. The second-order rate constant in the pH independent region can then be calculated from that measured at pH 5.85 and it is 1.33 $M^{-1}$ $s^{-1}$. The second-order rate constant of RA-42 in the pH independent region calculated from the measured pKa of 6.55 and the second-order rate constant at pH 5.85 is 0.305. Thus, the second-order rate constant of 4-methylimidazole in the pH independent region is 4.4 times greater than that of RA-42.

However, based on the Bronstedt relation (1), $$\log k_2 = \beta * pKa + A \quad (1)$$

($\beta$ is 0.8 for imidazole catalyzed hydrolysis of p-nitrophenylacetate; Bruice, T. C., et al., J. Am. Chem. Soc. 1959, 80, 2265–2267) and the above indicated pKa values, the second-order rate constant of 4-methylimidazole would be expected to be as much as 13.2 times greater than that of RA-42. Peptide RA-42 therefore catalyses the acylation of His-11 by a factor of 3, most likely by stabilization of the developing oxyanion in the transition state by the side chain of Orn-15.

As mentioned above, the observed rate enhancement of RA-42 over 4-methylimidazole at pH 5.85 is close to a factor 5. The extra rate enhancement is due to the fact that the stronger nucleophile 4-methylimidazole is protonated to a greater extent than the side chain of His-11. At pH 5.85, the concentration of unprotonated His-11 is 21 times greater than that of unprotonated 4-methylimidazole if the total concentration is the same. Thus, if the rate enhancement were due to the concentration effect alone, RA-42 would be a more efficient catalyst by a factor of 1.6 (21/13.2) at pH 5.85. The observed rate enhancement is therefore due to a transition state stabilization and pKa depression, two factors commonly encountered in naturally occurring catalysts.

Since the final product is an amide at the side chain of Orn-15, the second step of the reaction is an acyl group transfer in a fast intramolecular reaction from His-11 to the deprotonated form of Orn-15. The rate enhancement of the intramolecular reaction is high, since no trace of intermediate has been detected in the $^1$H NMR spectrum run under reaction conditions, but it can not be measured since the acylation of His-11 is the rate limiting step. A fast intramolecular reaction without accumulation of intermediate is also consistent with the observed first-order kinetics of RA-42.

As mentioned above, the histidine residue of RA-42 introduces a functional group at the side chain of Orn-15 in a highly selective reaction after which free histidine is regenerated. The other ornithine, Orn-34, does not form an amide and it has no neighboring histidine residue. Lys-10 which is next to His-11 and therefore close in space also does not form an amide under the reaction conditions.

The invention is, of course, not restricted to the embodiments specifically described above, but many modifications and chances may be made without departing from the general inventive concept as defined in the following claims.

```
                   SEQUENCE LISTING

SEQ ID NO:1
N-Aib-A-D-Nle-E-A-A-I-K-A-L-A-E-G-Nle-Aib-A-K
1                                             19

G-P-V-D
                                              20   23

G-Aib-R-A-F-A-E-F-A-K-A-L-Q-E-A-Nle-Q-A-Aib
42                                            24
                     SA-42

SEQ ID NO:2
N-Aib-A-D-Nle-E-A-A-I-K-H-L-A-E-Orn-Nle-Aib-A-K
1                                             19

G-P-V-D
                                              20   23

G-Aib-R-A-F-A-E-F-Orn-K-A-L-Q-E-A-Nle-Q-A-Aib
42                                            24
                     RA-42

SEQ ID NO:3
N-Aib-A-D-Nle-E-A-A-I-A-Orn-L-A-E-H-Nle-Aib-A-K
1                                             19

G-P-V-D
                                              20   23

G-Aib-R-A-F-A-E-F-Orn-A-A-L-Orn-E-A-Nle-Q-A-Aib
42                                            24
                     PA-42

SEQ ID NO:4
N-Aib-A-D-Nle-E-A-A-I-K-H-L-A-E-H-Nle-Aib-A-H
1                                             19

G-P-V-D
                                              20   23

G-Aib-R-A-F-A-E-F-H-K-A-L-H-E-A-Nle-H-A-Aib
42                                            24
                     KO-42
```

What is claimed is:

1. A method of performing a chemical reaction between a reagent and a substrate involving an acyl transfer mechanism comprising effecting said reaction in the presence of an imidazole-based catalyst capable of forming a transition complex with the substrate, wherein the catalytic imidazole function is provided by a chemical structure element comprising an optionally substituted imidazolyl group flanked on one or both sides by a group or groups capable of stabilizing the transition complex by molecular interaction with the acyl group.

2. The method of claim 1, where the molecular interaction is selected from hydrogen bonding, electrostatic interaction and hydrophobic interaction.

3. The method according to claim 1, wherein the flanking group or groups comprise a link or chain of from 1 to 6 chain atoms connected to a terminal group capable of said molecular interaction with the transition complex.

4. The method according to claim 1, wherein the pH conditions are selected such that at least part of the reagent to be reacted with the substrate in said acyl transfer reaction is protonated.

5. The method according to claim 1, wherein said flanking group is a positively charged hydrogen bond donor.

6. The method according to claim 1, wherein said chemical structure element has a rigid structure wherein the imidazolyl group and the flanking group or groups are arranged in a geometrically, relatively fixed relationship.

7. The method according to claim 1, wherein said chemical structure element is a peptide or polypeptide.

8. The method according to claim 1, wherein said imidazolyl function is provided by an optionally substituted histidine residue.

9. The method according to claim 7, wherein said chemical structure element is part of a synthetic protein or polypeptide.

10. The method according to claim 7, wherein said chemical structure element is of α-helix type, and a flanking group is arranged at position i+4 relative to an imidazolyl function at position i.

11. The method according to claim 7, wherein said chemical structure element is of α-helix type, and a flanking group is arranged at position i−3 relative to an imidazolyl function at position i.

12. The method according to claim 7, wherein said flanking group or groups are selected from histidine, ornithine, lysine and arginine.

13. The method according to claim 1, wherein said chemical structure element constitutes or is part of a larger structure having a functional group which is situated such that it is selectively functionalized with the substrate during acyl transfer as a result of an intramolecular reaction that occurs between said transition complex and the substrate.

14. The method according to claim 13, wherein said functional group is said flanking group or is one of said flanking groups.

15. The method according to claim 14, wherein said functional group is at position i+4 relative to an imidazolyl function at position i and is an ornithine, lysine or diaminobutyric acid residue.

16. The method according to claim 14, wherein said functional group is at position i−3 relative to an imidazolyl function at position i and is a lysine residue.

17. The method according to claim 15, wherein said functional groups are at both positions i+4 and i−3 relative to the imidazolyl function at position i.

18. The method according to claim 15, wherein more than one imidazolyl function is provided by the structural element and each imidazolyl function is optionally flanked on one or both sides by functional groups.

19. The method according to claim 18, wherein said functional groups are at positions i+4, j+4, or k+4 relative to the imidazolyl functions at positions i, j, or k.

20. The method according to claim 18, wherein said functional groups are at positions i−3, j−3, or k−3 relative to the imidazolyl functions at positions i, j, or k.

21. The method according to claim 18, wherein said functional group is selectively functionalized by a carbohydrate-containing residue.

22. The method according to claim 12, wherein the substrate is provided on a solid support, which immobilizes the chemical structure element to the support.

23. A synthetic chemical structure element as defined by claim 1.

24. A chemical catalyst which catalyzes reactions involving an acyl transfer mechanism wherein the catalyst comprises a chemical structure element as defined in claim 1.

25. A method of producing a protein or peptide which constitutes or comprises a synthetic chemical structure element as defined in claim 7, comprising transforming a host organism with a recombinant DNA construct comprising a vector containing a DNA sequence encoding said structure element, culturing the host organism to express said peptide, polypeptide or protein, and isolating the peptide, polypeptide, or protein from the culture.

26. A recombinant DNA construct comprising a vector containing a DNA sequence encoding a chemical structure element as defined in claim 7.

27. A method of introducing a desired chemical function at a specific position in a chemical compound comprising providing the chemical compound with a structure element as defined in claim 1, and reacting the compound with a substrate capable of providing the desired function.

28. A method according to claim 27, wherein the substrate comprises a carbohydrate residue.

29. The method of claim 3, wherein said link or chain is a $C_1$–$C_4$ alkyl.

30. The method of claim 9, wherein said protein or polypeptide comprises a helix-loop-helix structure.

31. The method of claim 17, wherein said functional groups are lysine residues.

32. The method according to claim 2, wherein the flanking group or groups comprise a link or chain of from 1 to 6 chain atoms connected to a terminal group capable of said molecular interaction with the transition complex.

33. The method according to claim 2, wherein the pH conditions are selected such that at least part of the reagent (to be) which is reacted with the substrate in said acyl transfer reaction is protonated.

34. The method according to claim 3, wherein the pH conditions are selected such that at least part of the reagent which is reacted with the substrate in said acyl transfer reaction is protonated.

35. The method according to claim 32, wherein the pH conditions are selected such that at least part of the reagent which is reacted with the substrate in said acyl transfer reaction is protonated.

36. The method according to claim 8, wherein said chemical structure element is part of a synthetic protein or polypeptide.

37. The method according to claim 8, wherein said chemical structure is of -helix type, and a flanking group is arranged at position i+4 relative to an imidazolyl function at position i.

38. The method according to claim 9, wherein said chemical structure is of -helix type, and a flanking group is arranged at position i+4 relative to an imidazolyl function at position i.

39. The method according to claim 15, wherein said functional group is at position i−3 relative to an imidazolyl function at position i and is a lysine residue.

40. The method according to claim 16, wherein said functional groups are at both positions i+4 and i−3 relative to the imidazolyl function at position i.

41. The method of claim 28, wherein said desired chemical compound is a polypeptide and the reaction with said carbohydrate residue-containing substrate protects such polypeptide from proteolytic degradation.

42. The method of claim 28, wherein said chemical compound is a polypeptide and the reaction with said carbohydrate residue-containing substrate facilitates the folding of said polypeptide.

43. The method of claim 17, wherein more than one group is selectively functionalized.

44. The method of claim 43, wherein more than one group is selectively functionalized by carbohydrate-containing residues.

45. A method for producing a vaccine comprising combining a compound produced according to claim 17, with a pharmaceutically-acceptable carrier.

46. The method of claim 32, wherein said link or chain is a $C_1$–$C_4$ alkyl group.

47. The method of claim 36, wherein said protein or polypeptide comprises a helix-loop-helix structure.

48. The method of claim 40, wherein said functional groups are lysine residues.

49. The method of claim 1, wherein said imidazole functional group is unprotonated.

50. A method for selecting a compound which mimics a naturally-occurring component of the immune system, comprising effecting the method of claim 1 under conditions which result in the production of at least one compound, and screening the resultant compounds to identify those which mimic a naturally occurring component of the immune system.

51. A method for selecting an antagonist compound which antagonizes a component of the immune system, comprising effecting the method of claim 1 under conditions which result in the production of at least one compound, and screening said at least one compound in order to identify an antagonist compound which antagonizes a component of the immune system.

52. A method for producing and selecting a compound which agonizes a component of the immune system, comprising effecting the method of claim 1 under conditions which result in the production of at least one compound, and selecting from among those compounds a compound which agonizes a component of the immune system.

53. A method for producing a structural element suitable for producing a compound which antagonizes an immune system component, comprising effecting the reaction of claim 1 under conditions which result in the production of at least one compound, and screening said at least one compound, to identify a compound which mimics a naturally-occurring component of the immune system, and utilizing said compound as a starting material to produce a compound which antagonizes an immune system component.

* * * * *

SEQUENCE LISTING

<160> NUMBER OF SEQ ID NOS: 4

<210> SEQ ID NO 1
<211> LENGTH: 42
<212> TYPE: PRT
<213> ORGANISM: Artificial Sequence
<220> FEATURE:
<221> NAME/KEY: MOD_RES
<222> LOCATION: (2)..(41)
<223> OTHER INFORMATION: Amino acids 2, 17, 24, and 41 are Xaa wherein
      Xaa = Aib (2-Aminoisobutyric acid).
<221> NAME/KEY: MOD_RES
<222> LOCATION: (5)..(27)
<223> OTHER INFORMATION: Amino acids 5, 16 and 27 are Xaa wherein Xaa =
      Nle (Norleucine).
<223> OTHER INFORMATION: Description of Artificial Sequence:catalysis of
      acyl transfer reactions

<400> SEQUENCE: 1

Asn Xaa Ala Asp Xaa Glu Ala Ala Ile Lys Ala Leu Ala Glu His Xaa
 1               5                  10                  15

Xaa Ala Lys Gly Pro Val Asp Xaa Ala Gln Xaa Ala Glu Gln Leu Ala
             20                  25                  30

Lys Ala Phe Glu Ala Phe Ala Arg Xaa Gly
         35                  40

<210> SEQ ID NO 2
<211> LENGTH: 42
<212> TYPE: PRT
<213> ORGANISM: Artificial Sequence
<220> FEATURE:
<221> NAME/KEY: MOD_RES
<222> LOCATION: (2)..(41)
<223> OTHER INFORMATION: Amino acids 2, 17, 24 and 41 are Xaa wherein
      Xaa = Aib (2-Aminoisobutyric acid).
<221> NAME/KEY: MOD_RES
<222> LOCATION: (5)..(27)
<223> OTHER INFORMATION: Amino acids 5, 16 and 27 are Xaa wherein Xaa =
      Nle (Norleucine).
<221> NAME/KEY: MOD_RES
<222> LOCATION: (15)..(34)
<223> OTHER INFORMATION: Amino acids 15 and 34 are Xaa wherein Xaa =
      Orn (ornithine).
<223> OTHER INFORMATION: Description of Artificial Sequence:catalysis of
      acyl transfer reactions

<400> SEQUENCE: 2

Asn Xaa Ala Asp Xaa Glu Ala Ala Ile Lys His Leu Ala Glu Xaa Xaa
 1               5                  10                  15

Xaa Ala Lys Gly Pro Val Asp Xaa Ala Gln Xaa Ala Glu Gln Leu Ala
             20                  25                  30

Lys Xaa Phe Glu Ala Phe Ala Arg Xaa Gly
         35                  40

<210> SEQ ID NO 3
<211> LENGTH: 42
<212> TYPE: PRT
<213> ORGANISM: Artificial Sequence
<220> FEATURE:
<221> NAME/KEY: MOD_RES
<222> LOCATION: (2)..(41)
<223> OTHER INFORMATION: Amino acids 2, 17, 24 and 41 are Xaa wherein
      Xaa = Aib (2-Aminoisobutyric acid).
<221> NAME/KEY: MOD_RES
<222> LOCATION: (5)..(27)
<223> OTHER INFORMATION: Amino acids 5, 16 and 27 are Xaa wherein Xaa =
      Nle (Norleucine).
<221> NAME/KEY: MOD_RES

```
<222> LOCATION: (11)..(34)
<223> OTHER INFORMATION: Amino acids 11, 30 and 34 are Xaa wherein Xaa =
      Orn (ornithine).
<223> OTHER INFORMATION: Description of Artificial Sequence:catalysis of
      acyl transfer reactions

<400> SEQUENCE: 3

Asn Xaa Ala Asp Xaa Glu Ala Ala Ile Ala Xaa Leu Ala Glu His Xaa
 1               5                  10                  15

Xaa Ala Lys Gly Pro Val Asp Xaa Ala Gln Xaa Ala Glu Xaa Leu Ala
             20                  25                  30

Ala Xaa Phe Glu Ala Phe Ala Arg Xaa Gly
         35                  40

<210> SEQ ID NO 4
<211> LENGTH: 42
<212> TYPE: PRT
<213> ORGANISM: Artificial Sequence
<220> FEATURE:
<221> NAME/KEY: MOD_RES
<222> LOCATION: (2)..(41)
<223> OTHER INFORMATION: Amino acids 2, 17, 24 and 41 are Xaa wherein
      Xaa = Aib (2-Aminoisobutyric acid).
<221> NAME/KEY: MOD_RES
<222> LOCATION: (5)..(27)
<223> OTHER INFORMATION: Amino acids 5, 16, 17, 24 and 27 are Xaa
      wherein Xaa = Nle (Norleucine).
<223> OTHER INFORMATION: Description of Artificial Sequence:catalysis of
      acyl transfer reactions

<400> SEQUENCE: 4

Asn Xaa Ala Asp Xaa Glu Ala Ala Ile Lys His Leu Ala Glu His Xaa
 1               5                  10                  15

Xaa Ala His Gly Pro Val Asp Xaa Ala Ala Xaa Ala Glu His Leu Ala
             20                  25                  30

Lys His Phe Glu Ala Phe Ala Arg Xaa Gly
         35                  40
```